United States Patent [19]

Uchino et al.

[11] Patent Number: 4,649,197

[45] Date of Patent: Mar. 10, 1987

[54] SULFATE OF 5,6,7,8-TETRAHYDRO-L-ERYTHRO-BIOPTERIN AND PROCESS FOR PREPARING THE SAME

[75] Inventors: Hayashi Uchino, Ako; Masaaki Azuma; Takehisa Ohashi, both of Kobe; Kiyoshi Watanabe, Akashi, all of Japan

[73] Assignee: Kanegafuchi Kagaku Kogyo Kabushiki, Osaka, Japan

[21] Appl. No.: 712,813

[22] Filed: Mar. 18, 1985

[30] Foreign Application Priority Data

Mar. 24, 1984 [JP] Japan .................. 59-56584

[51] Int. Cl.$^4$ ............................ C07D 475/04
[52] U.S. Cl. ................................. 544/258
[58] Field of Search ......................... 544/258

[56] References Cited

U.S. PATENT DOCUMENTS 3,468,886 9/1969 Mosher .................. 544/258
4,540,783 9/1985 Viscontini ............... 544/258
4,595,752 6/1986 Azuma .................... 544/258

FOREIGN PATENT DOCUMENTS 0487930 11/1952 Canada .................. 544/258

OTHER PUBLICATIONS

Matsuura Chemical Abstracts, 101:130486c, (1984).
S. W. Baily et al, *J. Biological Chem.*, 253, 1598 (1978).
Matsuura et al, *J. Biochem.* 87, 951 (1980).
M. Viscontini et al, *Helveta Chim. Acta*, 65, 1090 (1982).

*Primary Examiner*—Robert J. Warden
*Assistant Examiner*—Robert Benson
*Attorney, Agent, or Firm*—Armstrong, Nikaido, Marmelstein & Kubovcik

[57] ABSTRACT

A sulfate of tetrahydrobiopterin having the formula (I):

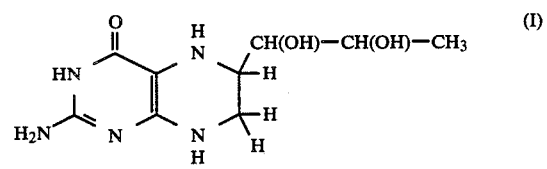

and a process for preparing the same, which comprises crystallizing tetrahydrobiopterin from an aqueous medium containing sulfuric acid. The sulfate of the (6R)-form of (1) has a high crystallinity and the process easily gives a sulfate of the (6R)-form.

10 Claims, 5 Drawing Figures

SULFATE OF 5,6,7,8-TETRAHYDRO-L-ERYTHRO-BIOPTERIN AND PROCESS FOR PREPARING THE SAME

BACKGROUND OF THE INVENTION

The present invention relates to a sulfate of 5,6,7,8-tetrahydro-L-erythro-biopterin (hereinafter referred to as "tetrahydrobiopterin") and a process for preparing the same.

In a living body, it has been well known that (6R)-tetrahydrobiopterin has a very important role as a coenzyme in a catecholamine-serotonin synthesis. Recently, the importance of (6R)-tetrahydrobiopterin has been recognized in the course of the fundamental study thereon. It has been expected that (6R)-tetrahydrobiopterin can be widely used for a treatment of patients with Parkinson's disease or depression as well as phenylketonuria which has been conventionally treated with (6R)-tetrahydrobiopterin.

In general, (6R)-tetrahydrobiopterin is synthesized by catalytically hydrogenating L-erythrobiopterin. In accordance with a conventional reaction condition, however, the (6S)-form being not present in nature is produced as a by-product at about 50% of the (6R)-form. Although a mixture of the (6R)-form and the (6S)-form hitherto has been obtained as a hydrochloride, it is difficult to separate the hydrochloride into each of its isomers by means of fractional crystallization. This is due to the poor crystallinity of tetrahydrobiopterin hydrochloride.

Then, there are proposed various methods, for instance, a method for separating the (6R)-form from the (6S)-form by employing high performance liquid chromatography (hereinafter referred to as "HPLC" (S. W. Baily et. al., "J. Biological Chem., 253, 1598 (1978); or Matsuura et. al.; "J. Biochem." 87, 951 (1980)); a method in which the (6R)-form is obtained by means of fractional crystallization of polyacylated tetrahydrobiopterin such as 2-N-acetyl 5,8-di-N-acetyl-1',2'-di-O-acetyl-5,6,7,8-tetrahydrobiopterin (M. Viscontini et. al., "Helv. Chim. Acta., 65, 1090 (1982)); and the like. However, a separating method by HPLC cannot be employed on an industrial scale, and in the fractional crystallization of polyacylated tetrahydrobiopterin, there are problems in that many reaction steps are required and the yield of the (6R)-form is low. Therefore, these methods are not utilizable.

An object of the present invention is to provide an easy process for preparing (6R)-tetrahydrobiopterin. A further object of the present invention is to obtain the (6R)-form in a high yield.

SUMMARY OF THE INVENTION

The present invention pertains to a sulfate of tetrahydrobiopterin having the formula (I):

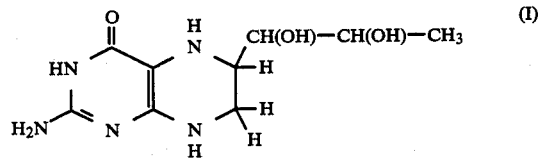

and a process for preparing a sulfate of tetrahydrobiopterin which comprises crystallizing tetrahydrobiopterin from an aqueous medium containing sulfuric acid. A sulfate of tetrahydrobiopterin prepared according to the present invention can be easily crystallized and is easily purified. Further the (6R)-form is prepared in a high yield by repeating the recrystallization of the sulfate due to the high crystallinity of the (6R)-form in comparison with the (6S)-form.

BRIEF DESCRIPTION OF THE DRAWINGS

In FIG. 1 and FIG. 2, the indications of "(6R)" and "(6S)" show the peaks for (6R)-tetrahydrobiopterin and (6S)-tetrahydrobiopterin, respectively.

DETAILED DESCRIPTION

Figure 1:
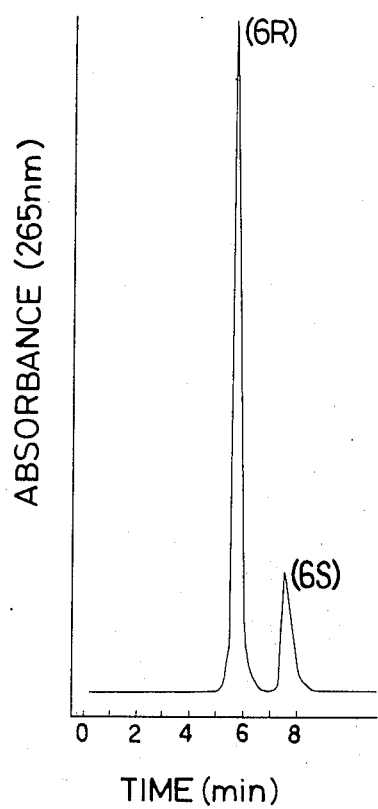
FIG. 1 is a chart of HPLC of the monosulfate of tetrahydrobiopterin prepared in Example 1.

The compound of the present invention is a sulfate of tetrahydrobiopterin having the formula (I):

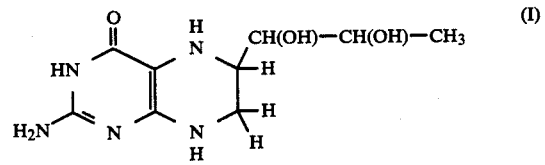

which has two diastereomers at the 6th carbon atom, that is to say, sulfates of (6R)-tetrahydrobiopterin and (6S)-tetrahydrobiopterin. The compound having the formula (I) is the (6R)-form, (6S)-form or a mixture thereof.

In the present invention, the molar ratio of tetrahydrobiopterin and sulfuric acid is 1:1, or the amount of sulfuric acid is not less than in the above ratio. For obtaining the effect of the present invention, however, it is sufficient to employ a monosulfate having the formula (II):

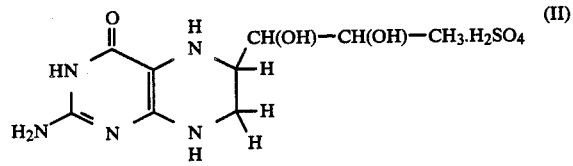

Even in the case where the amount of sulfuric acid is more than the above range, the same effect can be obtained as in the monosulfate.

In the present invention, the sulfate of tetrahydrobiopterin is prepared by crystallizing tetrahydrobiopterin as white needle crystals from an aqueous medium containing sulfuric acid. In that case, the concentration of tetrahydrobiopterin is 0.1 to 20% by weight (hereinafter referred to as "%") and the concentration of the added sulfuric acid is 1 to 10%. Examples of the aqueous medium are water, water-alcohol solution, and the like. Tetrahydrobiopterin is prepared by catalytically hydrogenating L-erythrobiopterin (hereinafter referred to as "biopterin"). The catalytic hydrogenation of biopterin can be carried out by means of conventional processes. For instance, there has been proposed a process in which tetrahydrobiopterin is prepared by catalytically hydrogenating biopterin in hydrochloric acid or trifluoroacetic acid in the presence of a platinum group catalyst such as Pt, Pd or Rh (Matsuura, "Tanpakushitsu Kakusan Koso", 26, 1934 (1981); M. Viscontini et. al., "Helv. Chim. Acta.", 61, 2731 (1978)).

The sulfate of tetrahydrobiopterin can be prepared by adding sulfuric acid into a solution including tetrahydrobiopterin obtained in the above process. In that case, it is preferable that the amount of sulfuric acid is 20 to 400% to the biopterin starting material, more preferably 40 to 200%.

Also, crystals of the sulfate of tetrahydrobiopterin can be obtained by converting a hydrochloride or trifluoroacetate of tetrahydrobiopterin obtained in the above conventional process in an aqueous sulfuric acid solution or water-alcohol solution including sulfuric acid into a sulfate.

Further, the sulfate of tetrahydrobiopterin can be also prepared by catalytically hydrogenating biopterin in an aqueous sulfuric acid solution.

In that case, it is preferable that the concentration of biopterin is 0.1 to 20% and the concentration of aqueous sulfuric acid solution is 1 to 10%. Examples of the catalyst are, for instance, platinum group catalysts such as Pt, Pd and Rh. The amount of the catalyst is 1 to 50% to biopterin.

The sulfate of tetrahydrobiopterin obtained in the above process can be fractionally crystallized from at least one member selected from the group consisting of water, alcohol and mineral acid. In that case, the concentration of the sulfate of tetrahydrobiopterin is 0.1 to 20%.

In the case that the mixed medium is a water-alcohol solution, it is preferable that the amount of alcohol is 5 to 50% by volume. Examples of the alcohol are, for instance, methanol, ethanol, propanol, butanol, and the like, preferably, methanol and ethanol. Also, it is possible to add a mineral acid into the water-alcohol solution. It is preferable that examples of the mineral acid are sulfuric acid, hydrochloric acid, and the like. The stability of the sulfate of tetrahydrobiopterin in the reaction mixture is increased by employing a mineral acid. It is preferable that the concentration of the mineral acid is 1 to 10%.

The sulfate of tetrahydrobiopterin thus obtained is generally a mixture of the (6R)-form and the (6S)-form. However, the sulfate of tetrahydrobiopterin which is rich in the (6R)-form can be obtained. This result is based upon the higher crystallinity of the (6R)-form in comparison with the (6S)-form. Further, the sulfate of tetrahydrobiopterin which contains at least 98% of the (6R)-form can be obtained by repeating the above fractional crystallization.

The present invention takes advantage of the characteristic crystallization of the sulfate of tetrahydrobiopterin. In contrast, in the hydrochloride of tetrahydrobiopterin, fractional crystallization does not smoothly proceed as shown in the Reference Example.

The optimum process for utilizing the characteristic crystallization of the sulfate of tetrahydrobiopterin is a process in which tetrahydrobiopterin being rich in the (6R)-form and being prepared by the hydrogenation process of biopterin improved by the present inventors ("Process for preparing 5,6,7,8-tetrahydro-6-(L-erythro-1',2'-dihydroxypropyl)pterin", Japanese patent application No. 56584/1984) is converted into the sulfate and then the sulfate is crystallized. In such a process, when biopterin is catalytically hydrogenated in a basic medium in the presence of a platinum group catalyst, the (6R)/(6S) ratio (ratio of the (6R)-form to the (6S)-form of tetrahydrobiopterin, hereinafter the same) of the prepared tetrahydrobiopterin is 6 to 9 and a reaction mixture having tetrahydrobiopterin which is rich in the (6R)-form can be obtained. In case that the sulfate of tetrahydrobiopterin is prepared by adding sulfuric acid to the reaction mixture thus obtained, the sulfate of tetrahydrobiopterin can be obtained in a high yield, and also the sulfate of tetrahydrobiopterin which is rich in the (6R)-form can be obtained as needle crystals.

In such case, the amount of sulfuric acid is at least an amount capable neutralizing a base such as potassium carbonate in a basic medium and thereto there is further added sulfuric acid of an amount capable of forming a sulfate with the produced tetrahydrobiopterin. Thus, after the reaction mixture is acidified with sulfuric acid, the acidified solution is concentrated and an inorganic salt is filtered off. Then, the filtrate is allowed to cool or an alcohol such as ethanol is added to the filtrate to deposit the sulfate of tetrahydrobiopterin.

Also, after tetrahydrobiopterin prepared in a basic medium is converted into a hydrochloride of tetrahydrobiopterin by adding hydrochloric acid, the hydrochloride is dissolved in an aqueous sulfuric acid solution or water-alcohol solution having sulfuric acid to deposit the sulfate of tetrahydrobiopterin. In such case, the amount of sulfuric acid is 0.1 to 20%, preferable 1 to 10%.

As mentioned above, in the present invention, it is possible to easily obtain (6R)-tetrahydrobiopterin.

The present invention is more specifically described and explained by means of the following Examples, in which all % is by weight unless otherwise noted. It is to be understood that the present invention is not limited to the Examples, and various changes and modifications may be made in the invention without departing from the spirit and scope thereof.

EXAMPLE 1

There was dispersed 100 mg of platinum oxide into 50 ml of a 1N hydrochloric acid, and then hydrogen gas was passed through the resulting dispersion to activate the catalyst. Fifty milliliters of 1N hydrochloric acid solution containing 1 g of biopterin was added to the above dispersion. A catalytic reduction was conducted by agitating the resulting mixture for 3 hours under normal temperature and normal pressure in a hydrogen atmosphere. After the completion of the reduction, the catalyst was filtered off from the reaction mixture, and the resulting filtrate was analyzed by employing a HPLC (column: Whatman Partisil 10 SC X 4 X 250 mm; eluent: 30 mM $NH_4H_2PO_4(H_3PO_4)$, pH 3.0). The (6R)/(6S) ratio of hydrochloride of tetrabiopterin solution thus obtained was 58/42.

Ten milliliters of 10% aqueous sulfuric acid solution was added into the above hydrochloride solution, and further 20 ml of ethanol was added into the solution. The mixed solution was allowed to stand in a cool and dark place for one day to deposit white needle crystals. The crystals were filtered off from the reaction mixture and dried to give 1.0 g of sulfate of tetrahydrobiopterin.

The (6R)/(6S) ratio of the sulfate thus obtained was 78/22 as measured by HPLC.

The chart of HPLC is shown in FIG. 1.

Elementary Analysis: Found (%): C 31.11; H 5.06; N 19.80; S 10.1. Calcd. (%): C 31.85; H 5.04; N 20.63; S 9.44.

From the result of the elementary analysis, it was confirmed that the produced crystals were monosulfate of tetrahydrobiopterin.

EXAMPLE 2

Ten milligrams of platinum oxide was dispersed into 10 ml of 10% aqueous solution of potassium carbonate, and then the catalyst was activated with hydrogen gas. Then, 10 ml of 10% aqueous solution of potassium carbonate containing 50 mg of biopterin was added to the above dispersion. After the catalytic reduction was conducted by agitating the resulting mixture for 10 hours under normal temperature and normal pressure in a hydrogen atmosphere, the reaction mixture was adjusted to pH 1 by adding 2N hydrochloric acid, and then the catalyst was filtered off from the reaction mixture.

The (6R)/(6S) ratio of the reaction solution thus obtained was 86/14 as measured by HPLC. After the reaction mixture was concentrated to 5 ml, 10 ml of ethanol was added to the concentrated solution. The deposited potassium chloride was filtered off from the concentrated solution. Then, 2 ml of 10% sulfuric acid was added to the filtrate and the mixed filtrate was allowed to stand in a cool and dark place to deposit white needle crystals. The crystals were filtered off from the above filtrate and dried to give 60 mg of sulfate of tetrahydrobiopterin. The (6R)/(6S) ratio of the sulfate thus obtained was 93/7 as measured by HPLC.

EXAMPLE 3

There was dispersed 100 mg of platinum oxide into 100 ml of a 1N hydrochloric acid, and then the catalyst was activated with hydrogen gas. Then, 100 ml of 1N hydrochloric acid solution containing 1 g of biopterin was added to the above dispersion. After the catalytic reduction was conducted for 5 hours under normal temperature and normal pressure in a hydrogen atmosphere, the catalyst was filtered off from the reaction mixture to give a hydrochloric acid solution of tetrahydrobiopterin having a (6R)/(6S) ratio of 60/40 as measured by HPLC. Light yellow powder was produced by repeating the cycle of concentration of the solution and addition of ethanol. The powder was filtered off from the above solution to give 1.08 g of powder. The (6R)/(6S) ratio of the powder thus obtained was 57/43 as measured by HPLC.

One gram of the obtained hydrochloride of tetrahydrobiopterin was dissolved in 30 ml of water, and 10 ml of 10% aqueous sulfuric acid solution was added to the dissolved solution to deposit soon white needle crystals. The obtained crystals were filtered off from the dissolved solution and dried to give 0.65 g of sulfate of tetrahydrobiopterin. The (6R)/(6S) ratio of the sulfate thus obtained was 80/20 as measured by HPLC.

EXAMPLE 4

Ten milligrams of palladium oxide was dispersed into 10 ml of 5% aqueous sulfuric acid solution, and then the catalyst was activated with hydrogen gas. Then, 10 ml of 5% aqueous sulfuric acid solution containing 50 mg of biopterin was added to the above dispersion. After the catalytic reduction was conducted by agitating the resulting mixture for 3 hours under normal temperature and normal pressure in a hydrogen atmosphere, the catalyst was filtered off from the reaction mixture to give a sulfuric acid solution of tetrahydrobiopterin having a (6R)/(6S) ratio of 70/30 as measured by HPLC.

Then, 10 ml of ethanol was added to the filtrate and the mixed filtrate was allowed to stand in a cool and dark place for one night to deposit white needle crystals. The crystals were filtered off from the above filtrate and dried to give 42 mg of sulfate of tetrahydrobiopterin. The (6R)/(6S) ratio of the sulfate thus obtained was 90/10 as measured by HPLC.

EXAMPLE 5

Ten milligrams of platinum black was dispersed into 10 ml of 10% aqueous solution of potassium carbonate, and then the catalyst was activated with hydrogen gas. Then, 10 ml of 10% aqueous solution of potassium carbonate containing 50 mg of biopterin was added to the above dispersion. After the catalytic reduction was conducted by agitating the resulting mixture for 20 hours under normal temperature and normal pressure in a hydrogen atmosphere, the reaction mixture was adjusted to pH 1 by adding 20 ml of 10% aqueous solution of sulfuric acid. The catalyst was filtered off from the reaction mixture to give a solution of tetrahydrobiopterin having a (6R)/(6S) ratio of 90/10 as measured by HPLC.

The obtained solution was concentrated, and the deposited inorganic salt was filtered off from the solution, and the filtrate was allowed to stand in a cool and dark place to deposit white needle crystals. The crystals were filtered off from the above filtrate and dried to give 58 mg of sulfate of tetrahydrobiopterin. The (6R)/(6S) ratio of the sulfate thus obtained was 95/5 as measured by HPLC.

EXAMPLE 6

There was dissolved 0.5 g of sulfate of tetrahydrobiopterin having a (6R)/(6S) ratio of 92/8 in 200 ml of water by heating, and then the obtained solution was allowed to stand in a cool and dark place for one day to deposit white needle crystals. The crystals were filtered off from the above solution and dried to give 0.42 g of sulfate of tetrahydrobiopterin. The (6R)/(6S) ratio of the crystals thus obtained was 97/3 as measured by HPLC.

There was obtained 0.30 g of white needle crystals of monosulfate of (6R)-tetrahydrobiopterin having less than 2% of the (6S)-form of by repeating the above-mentioned procedures of recrystallization 2 times.

Figure 2:
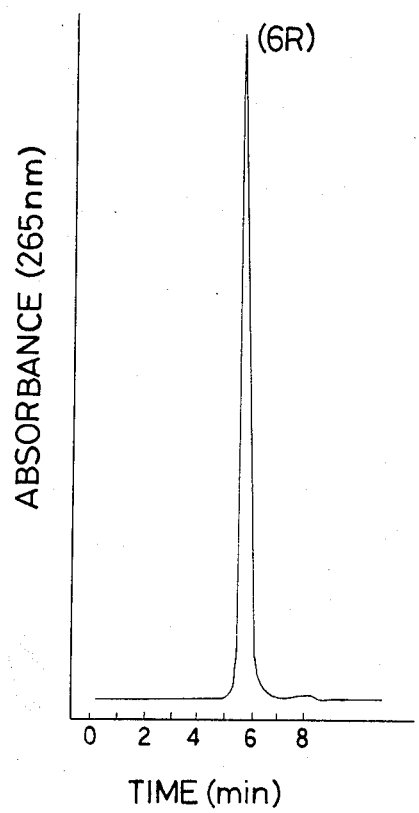
FIG. 2 is a chart of HPLC of the monosulfate of tetrahydrobiopterin prepared in Example 6.

The chart of HPLC is shown in FIG. 2.

Elementary Analysis: Found (%): C 31.56; H 5.04; N 20.30; S 9.90. Calcd. (%): C 31.85; H 5.04; N 20.63; S 9.44.

Figure 3:
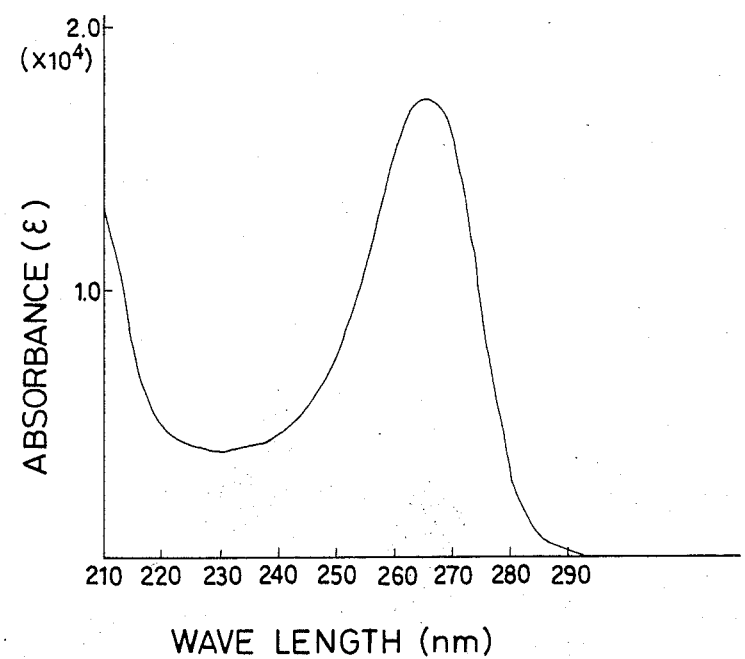
FIG. 3 is a chart of the ultraviolet absorption spectrum of the monosulfate of tetrahydrobiopterin prepared in Example 6.
Figure 4:
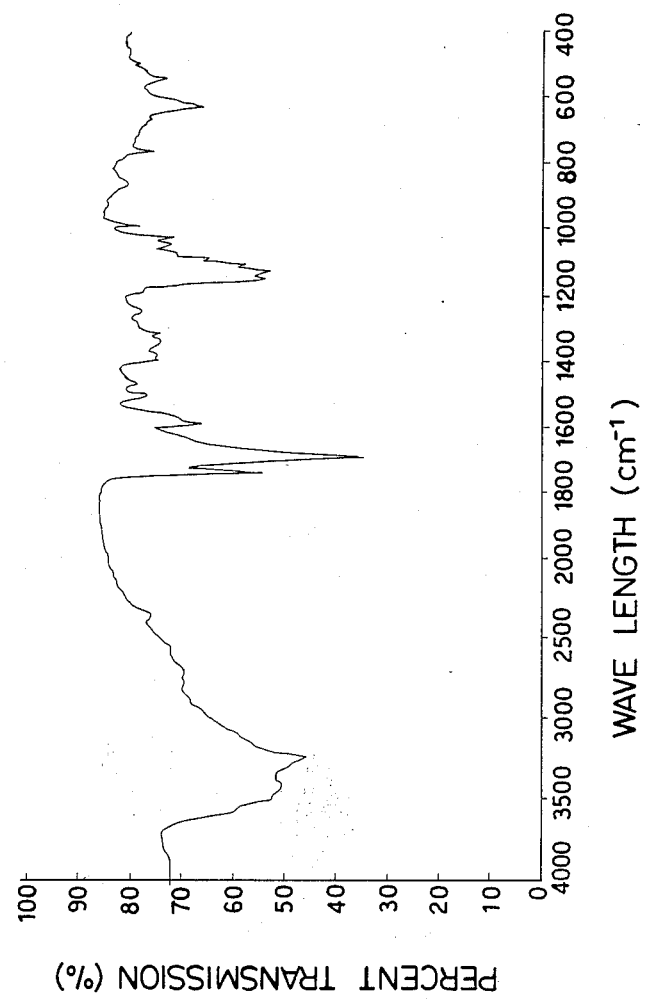
FIG. 4 is a chart of the infrared absorption spectrum of the monosulfate of tetrahydrobiopterin prepared in Example 6.

The ultraviolet absorption spectrum ($C=1.2\times10^{-3}$; 1N HCl) (the chart of the ultraviolet absorption spectrum is shown in FIG. 3) and the infrared absorption spectrum (the chart of the infrared absorption spectrum is shown in FIG. 4) show a monosulfate of tetrahydrobiopterin $[\alpha]_D^{20}$ was $-6.7°$ ($C=0.12$; 1N HCl); $-6.4°$ ($C=0.5$; 1N HCl). The crystals did not have an obvious melting point and the reduction of weight of the crystals was observed from about 215° C. by thermobalance analysis. $^1$H-NMR spectrum analysis (60 MHz, 20% DCl):

3.60 to 4.20 (m. H-C (6,7,1',2')), 1.42 (d, J=6 Hz, 3H-C(3')).

Figure 5:
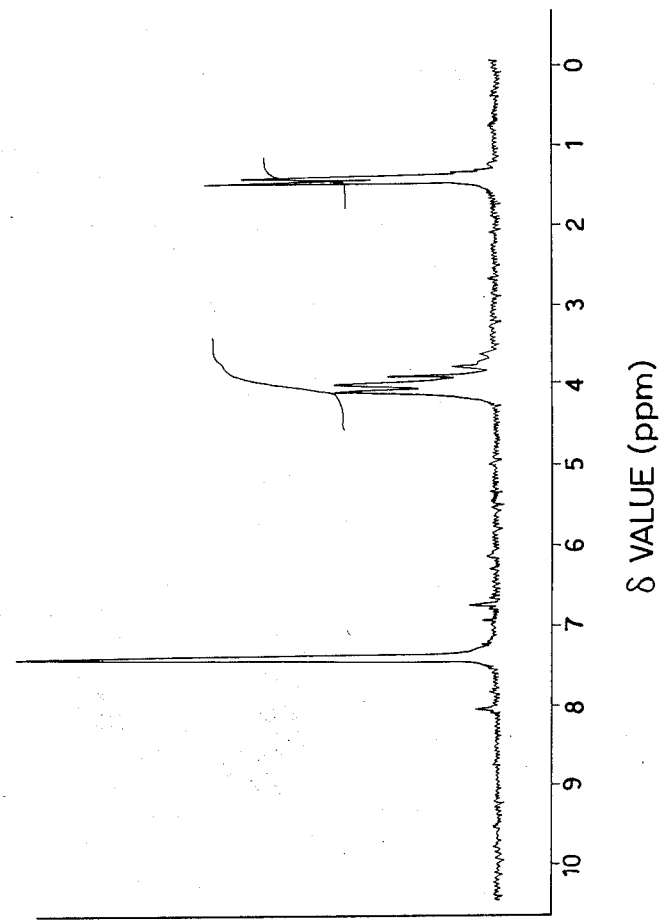
FIG. 5 is a chart of $^1$H-NMR of the sulfate of tetrahydrobiopterin prepared in Example 6.

The chart of $^1$H-NMR spectrum is shown in FIG. 5.

COMPARATIVE EXAMPLE

There was dispersed 500 mg of platinum oxide into 250 ml of 10% aqueous solution of potassium carbonate, and then the catalyst was activated with hydrogen gas. Then, 250 ml of 10% aqueous solution of potassium carbonate containing 5.0 g of biopterin was added to the above dispersion. After the catalytic reduction was conducted by agitating the resulting mixture for 5 hours under normal temperature and normal pressure in a hydrogen atmosphere, the reaction mixture was adjusted to pH 1 by adding 2N hydrochloric acid. The catalyst was filtered off from the reaction mixture to give tetrahydrobiopterin solution having a (6R)/(6S) ratio of 80/20 as measured by HPLC.

After the obtained solution was concentrated to about 100 ml, 100 ml of ethanol was added to the concentrated solution to deposit an inorganic salt, and then the salt was filtered off from the concentrated solution.

Light yellow crystals of hydrochloride of tetrahydrobiopterin were produced by repeating the cycle of concentration of the filtrate and addition of ethanol. The crystals were filtered off from the above filtrate and dried to give 3.15 g of crystals having a (6R)/(6S) ratio of 80/20 as measured by HPLC.

Further, the filtrate was concentrated and ethanol was added to the concentrated filtrate to produce light yellow crystals. The crystals were filtered off from the above filtrate and dried to give 1.35 g of crystals having a (6R)/(6S) ratio of 79/21.

Further, 1.2 g of crystals having a (6R)/(6S) ratio of 93/7 were obtained by means of the above-mentioned procedure.

In addition to the ingredients employed in Examples, other ingredients can be employed in Examples as set forth in the specification to obtain substantially the same results.

What we claim is:

1. A monosulfate of 5,6,7,8-tetrahydro-L-erythrobiopterin having the formula (II):

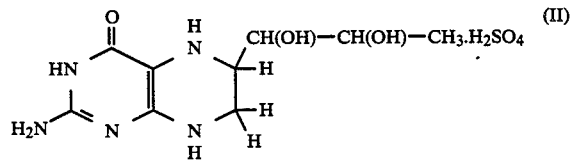

2. The sulfate of claim 1, wherein said 5,6,7,8-tetrahydro-L-erythro-biopterin is a mixture of the (6R)-form and the (6S)-form.

3. The sulfate of claim 1, wherein said 5,6,7,8-tetrahydro-L-erythro-biopterin is the (6R)-form.

4. A process for preparing a monosulfate of a diastereoisomer at the 6-position of 5,6,7,8-tetrahydro-L-erythhro-biopterin having the formula (I):

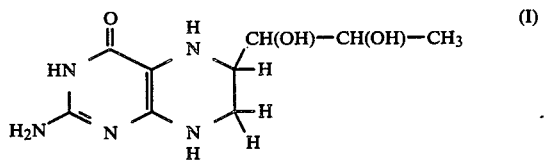

which comprises subjecting a mixture of the (6R)-form and the (6S)-form of 5,6,7,8-tetrahydro-L-erythrobiopterin to crystallization from an aqueous medium containing sulfuric acid, and separating from the aqueous medium a crystallized mixture of the (6R)-form and the (6S)-form of the monosulfate of 5,6,7,8-tetrahydro-L-erythro-biopterin, said mixture being enriched in the (6R)-form.

5. The process of claim 4, wherein the diastereoisomer at the 6-position is the (6R)-form having the formula (III):

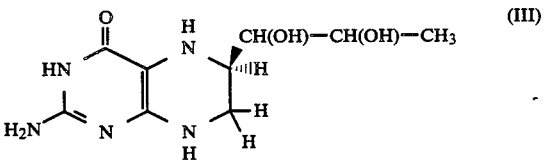

6. The process of claim 5, wherein said mixture of the (6R)-form and the (6S)-form of the monosulfate is further subjected to fractional crystallization from at least one member selected from the group consisting of water, alcohol and a strong mineral acid to give a monosulfate further enriched in the (6R)-form.

7. The process of claim 5 or 6, wherein said mixture of the (6R)-form and the (6S)-form of 5,6,7,8-tetrahydro-L-erythro-biopterin is prepared by catalytically hydrogenating L-erythro-biopterin in the presence of a platinum group catalyst selected from the group consisting of Pt, Pd and Rh.

8. The process of claim 7, wherein said catalytic hydrogenation is carried out in an aqueous solution of sulfuric acid.

9. The process of claim 7, wherein said catalytic hydrogenation is carried out in a basic medium.

10. The process of claim 4, wherein a monosulfate of the (6S)-form of 5,6,7,8-tetrahydro-L-erythro-biopterin is recovered from the aqueous medium after the (6R)-form is separated.

* * * * *

UNITED STATES PATENT AND TRADEMARK OFFICE
CERTIFICATE OF CORRECTION

PATENT NO. : 4,649,197
DATED : March 10, 1987
INVENTOR(S) : HAYASHI UCHINO ET AL It is certified that error appears in the above-identified patent and that said Letters Patent is hereby corrected as shown below:

On the cover page, Item [73], after "Kabushiki" insert --- Kaisha ---.

Signed and Sealed this

Twenty-fifth Day of August, 1987

Attest:

DONALD J. QUIGG

Attesting Officer        Commissioner of Patents and Trademarks